United States Patent [19]

Hoyer et al.

[11] Patent Number: 5,817,466
[45] Date of Patent: Oct. 6, 1998

[54] CONSERVED YEAST NUCLEIC ACID SEQUENCES

[75] Inventors: Lois L. Hoyer, Amea, Iowa; George P. Livi; Allan R. Shatzman, both of King of Prussia, Pa.

[73] Assignee: SmithKline Beecham Corporation, Philadelphia, Pa.

[21] Appl. No.: 878,106

[22] Filed: Jun. 18, 1997

Related U.S. Application Data

[62] Division of Ser. No. 357,962, Dec. 16, 1994, Pat. No. 5,668,263.

[51] Int. Cl.[6] .............................. C12Q 1/68; C07H 1/02; C07H 1/04
[52] U.S. Cl. .............................. 435/6; 536/23.1; 536/24.3
[58] Field of Search ................................ 435/6; 536/23.1, 536/24.3; 935/77, 78

[56] References Cited

U.S. PATENT DOCUMENTS

| | | | |
|---|---|---|---|
| 5,332,660 | 7/1994 | Takeda et al. | 435/6 |
| 5,403,710 | 4/1995 | Weisburg et al. | 435/6 |
| 5,405,745 | 4/1995 | Gorman et al. | 435/6 |
| 5,426,026 | 6/1995 | Jordan | 435/6 |
| 5,426,027 | 6/1995 | Lott et al. | 435/6 |
| 5,489,513 | 2/1996 | Springer et al. | 435/6 |
| 5,529,916 | 6/1996 | Cormack et al. | 435/195 |
| 5,545,525 | 8/1996 | Montplaisir et al. | 435/6 |
| 5,645,992 | 7/1997 | Lott et al. | 435/6 |
| 5,668,262 | 9/1997 | Hoyer et al. | 536/23.1 |

OTHER PUBLICATIONS

Cutler et al., J. Clinical Microbiology 26 (9) : 1720–1724 (1988).

Holmes et al., J. Clinical Microbiology 32 (1) : 228–231 (1994).

Miyakawa et a., J. Clinical Microbiology 30 (4) : 894–900 (1992).

*Primary Examiner*—W. Garin Jonex
*Assistant Examiner*—Ethan Whisenant
*Attorney, Agent, or Firm*—Edward R. Gimmi; William T. King; Edward T. Lentz

[57] ABSTRACT

This invention relates to nucleic acid sequences conserved in strains of yeasts. More particularly, this invention relates to segments of the ALS1 gene of *Candida albicans* useful as probes and primers for the identification of yeast, particularly Candida, infections.

16 Claims, 7 Drawing Sheets

```
CCAAATCCAA CTGTTAGTAC TACTGAATAT TGGTCTCAGT...//
CCAAACCATA CTGTCACTAC TACTGAATAT TGGTCACAAT...//
CCAAATCCAA CTGTCACTAC AACCGAGTAT TGGTCTCAAT...//
CCAAACCCAA CTGTCACCAC CACTGAATAT TGGTCCCAAT...//
CCAAACCACA CTGTCACTAC TACTGAATAC TGGTCACAAT...//
CCAAACCACA CTGTCACTAC TACTGAGTAT TGGTCTCAAT...//
CCAAACCCAA CTGTCACCAC TACTGAATAC TGGTCTCAAT...//
CCAAACCATA CTGTCACTAC TACTGAATAC TGGTCTCAAT...//
CCAAACCATA CTGTCACTAC TACTGAATAC TGGTCTCAAT...//
CCAAATCCAA CAGTTACTAC TACTGAATAT TGGTCACAAT...//
```

Consensus
```
CCAAA C   A C GT A  AC   AC GA TA    TGGTC CA  T...//
CCAAA C   A CTGT AC AC   ACT GA TA   TGGTC  CAAT...//
```

```
CCTTTGCTAC AACCACTACA GTTACTGCTC CTCCAGGTGG...//
CCTTTGCTAC TACTACTACT GTTACTGCTC CTCCAGGTGG...//
CCTTTGCTAC TACTACTACA GTTACTGCTC CTCCAGGTGG...//
CTTACGCAAC CACAACTACT GTGACTGCTC CTCCAGGAGG...//
CATATGCCAC CACTACCACT GTAACTGCAC CACCAGGTGG...//
CGTTTGCTAC TACCACAACT GTAACTGGTC CACCAAGTGG...//
CATATGCAAC CACTACTACC ATTACCGCTC CACCTGGTGA...//
CATATGCTAC AACCACCACT GTTACTGCAC CACCTGGTGA...//
CATATGCTAC AACCACCACT GTTACTGCAC CACCAGGTGG...//
CATTTGCCAC AACCACCACA GTTACTGCTC CTCCAGGTGG...//
```

Consensus
```
C T  GC AC   AC AC AC    T AC G C C  CC   G G  ...//
C T TGC AC   AC AC AC   GT ACTGC C C  CC  GGAG ...//
```

```
TACCGATACT GTGATTATCA GAGAGCCA
TACTGACTCA GTAATTATCA GAGAACCA
TACTGACTCA GTAATTATCA GAGAACCT
CACTGACTCA GTAATTATCA GAGAACCA
TACTGACACT GTTATTATTA GAGAGCCA
CACTGATACT GTTATCATTA GGGAACCA
AACTGATACC GTTCTCATCA GAGAGCCA
AACCGATACC GTTCTTATCA GAGAGCCA
TACCGATACT GTTATCATTA GAGAGCCA
TACTGACACT GTGATTATC
```

FIG. 3A

Consensus
```
 AC GA   C GT  T AT A G GA CC
 AC GA   C GT  T AT A GAGA CCA
```

```
PNPTVSTTEYWSQSFATTTTVTAPPGGTDTVIIREP
PNHTVTTTEYWSQSFATTTTVTAPPGGTDSVIIREP
PNPTVTTTEYWSQSFATTTTVTAPPGGTDSVIIREP
PNPTVTTTEYWSQSYATTTTVTAPPGGTDSVIIREP
PNHTVTTTEYWSQSYATTTTVTAPPGGTDTVIIREP
PNHTVTTTEYWSQSFATTTTVTGPPSGTDTVIIREP
PNPTVTTTEYWSQSYATTTTITAPPGETDTVLIREP
PNHTVTTTEYWSQSYATTTTVTAPPGETDTVLIREP
PNHTVTTTEYWSQSYATTTTVTAPPGGTDTVIIREP
PNPTVTTTEYWSQSFATTTTVTAPPGGTDTVII
```

Consensus
```
PN TV TTEYWSQS ATTTT T PP   TD V  IREP
PN TVTTTEYWSQS ATTTTVTAPPG TD V  IREP
```

FIG. 3B

CCAAATCCAA CTGTTAGTAC TACTGAATAT TGGTCTCAGT...//
CCAAACCATA CTGTCACTAC TACTGAATAT TGGTCACAAT...//
CCAAATCCAA CTGTCACTAC AACCGAGTAT TGGTCTCAAT...//
CCAAACCCAA CTGTCACCAC CACTGAATAT TGGTCCCAAT...//
CCAAACCACA CTGTCACTAC TACTGAATAC TGGTCACAAT...//
CCAAACCACA CTGTCACTAC TACTGAGTAT TGGTCTCAAT...//
CCAAACCCAA CTGTCACCAC TACTGAATAC TGGTCTCAAT...//
CCAAACCATA CTGTCACTAC TACTGAATAC TGGTCTCAAT...//
CCAAACCATA CTGTCACTAC TACTGAATAC TGGTCTCAAT...//
CCAAATCCAA CAGTTACTAC TACTGAATAT TGGTCACAAT...//

CCTTTGCTAC AACCACTACA GTTACTGCTC CTCCAGGTGG...//
CCTTTGCTAC TACTACTACT GTTACTGCTC CTCCAGGTGG...//
CCTTTGCTAC TACTACTACA GTTACTGCTC CTCCAGGTGG...//
CTTACGCAAC CACAACTACT GTGACTGCTC CTCCAGGAGG...//
CATATGCCAC CACTACCACT GTAACTGCAC CACCAGGTGG...//
CGTTTGCTAC TACCACAACT GTAACTGGTC CACCAAGTGG...//
CATATGCAAC CACTACTACC ATTACCGCTC CACCTGGTGA...//
CATATGCTAC AACCACCACT GTTACTGCAC CACCTGGTGA...//
CATATGCTAC AACCACCACT GTTACTGCAC CACCAGGTGG...//
CATTTGCCAC AACCACCACA GTTACTGCTC CTCCAGGTGG...//

TACCGATACT GTGATTATCA GAGAGCCA
TACTGACTCA GTAATTATCA GAGAACCA
TACTGACTCA GTAATTATCA GAGAACCT
CACTGACTCA GTAATTATCA GAGAACCA
TACTGACACT GTTATTATTA GAGAGCCA
CACTGATACT GTTATCATTA GGGAACCA
AACTGATACC GTTCTCATCA GAGAGCCA
AACCGATACC GTTCTTATCA GAGAGCCA
TACCGATACT GTTATCATTA GAGAGCCA
TACTGACACT GTGATTATC

SEQ. I.D. NO.: 1

FIG. 5A

CCAAAYCMHA CWGTYASYAC HACYGARTAY TGGTCNCART

CNTWYGCHAC HACHACHACH RTDACYGSWC CWCCWRGWGR

HACYGAYWCH GTDMTYATYA GRGARCCW

SEQ. ID. NO:2

CCAAAYCMHA CWGTYASYAC

SEQ.ID. NO:3

WGGYTCYCTR ATRAKHACDG

SEQ. ID. NO:4

GATATCGAATTCGCGGCCGCGTCACAATCATATGCCACCAC
TACCACTGTAACTGCACCACCAGGTGGTACTGACACTGTTA
TCATTAGAGAGCCACCAAACCATACTGTCACCACTACTGAA
TACTGGTCTCAGTCCTATGCAACCACTACTACCATTACCGC
TCCACCTGGTGAAACCGATACCGTTCTTATCAGAGAGCCAC
CAAACCATACTGTCACTACTACTGAATACTGGTCTCAATCA
TATGCTACAACCACCACTGTTACTGCACCACCAGGAGGTAC
CGATACTGTTATCATTAGAGAGCCACCAAATCCAACAGTTA
CTACTACTGAATATTGGTCACAATCATTTGCCACAACCACC
ACAGTTACTGCTCCTCCAGGTGGTACTGACACTGTGATTAT
CTATGAAAGCATGT

SEQ. I.D. NO.: 5

FIG. 5B

CONSERVED YEAST NUCLEIC ACID SEQUENCES

This is a Divisional of application Ser. No. 08/357,962, filed Dec. 16, 1994, now U.S. Pat. No. 5,668,263.

FIELD OF THE INVENTION

This invention relates to nucleic acid sequences conserved in strains of yeasts. More particularly, this invention relates to segments of the ALS1 gene of *Candida albicans* useful as probes and Polymerase Chain Reaction (PCR) primers for the identification of yeast, particularly Candida, infections.

BACKGROUND OF THE INVENTION

Nucleic acid-based methods for the detection of microbes in clinical samples can be separated into two broad categories, differing primarily in the lower limit of detection of the target nucleic acid sequence. The first category employs conventional molecular techniques to detect target sequences directly from clinical samples or subcultured microbial isolates. The second category, predicated on nucleic acid amplification technologies, rapidly enriches the target sequences prior to detection thereby bypassing the time, effort and expense of subculturing an isolate prior to analysis. The determination of which approach to employ depends on a number of factors such as cost, labor and the clinical need for rapid results. The nucleic acid molecules of this invention may be advantageously employed in either of the two systems.

Conventional methods for nucleic acid detection rely on physio-chemical methods to foster visualization of the molecules or rely on hybridization methodology employing nucleic acid probes which are labelled with analytically detectable reagents. Examples include: plasmid profiling whereby plasmid DNAs are isolated from microbial isolates and separated by molecular weight by agarose gel electrophoresis; Southern blotting whereby endonuclease-digested DNA is immobilized on supports such as nitrocellulose filters then probed with analytically labeled nucleic acid to detect specific complementary sequences. Analytically detectable reagents for this purposes include radioactive isotopes (e.g., $^{14}C$ and $^{32}P$) and non-radioactive reagents such as chemiluminescent materials; DNA dot blots whereby DNA is extracted from a number of microbial isolates by any convenient means and transferred by vacuum filtration to a support and probed as is the case of Southern blotting; and Colony dot blots whereby the colonies are cultured on agar plates, transferred to paper and lysed in situ prior to probing.

Amplification systems rely on the existence of primer nucleic acid molecules of 10–30 nucleotides in length which flank the target region. The primer acts as initiation points for multiple cycles of DNA replication on the region defined by the flanking primers. The Polymerase Chain Reaction employing the Taq DNA polymerase (Mullis and Faloona, *Meth. Enzymol.* 155:335–350(1987)) is a classic example of an amplification system.

Candida species are well known human pathogens that have been associated with a number of disease states. Most recently, a major concern is hematogenously disseminated infection which is occurring with increased prevalence in postoperative and immunocomprised patients. Identification of such infection can take a minimum of 2 days with an optimal blood culture system, so there is a need for a rapid, sensitive, and specific test to aid in the diagnosis of the disseminated yeast infections. DNA-based diagnostic tests not only are sensitive and specific but also have the potential to decrease the time taken for the laboratory identification of pathogens that are slowly growing or difficult to culture. Early detection and identification of the infecting species in blood or biopsies would facilitate prompt, appropriate treatment.

A number of DNA sequences that are unique to *Candida albicans* and that may be suitable for diagnostic use have been identified. For example, sequences encoding cytochrome P-450 lanosterol-14α-demethylase (Buchman, T. G. et al., *Surgery* 108:338–347 (1990)), mitochondrial DNA (Miyakawa, Y., et al., *J. Clin. Microbiol.* 30:894–900(1992)), and the secreted aspartyl proteinase (Kanaizuka, I. et al., *Jpn. J. Med. Mycol.* 34:19–26(1993)) have been used in the PCR-based detection of *C. albicans* in blood, urine, or cerebrospinal fluid. Nucleic acid probes that hybridize to repeated sequences of *C. albicans* DNA may provide additional sensitivity, especially when combined with PCR amplification. Recently two DNA fragments were described from the rDNA (genes coding for rRNA) repeat unit of *C. albicans* for use as DNA probes to detect *C. albicans* or other yeasts (Holmes, A. R. et al., *J. Med. Microbiol.* 37:346–351(1992)). One probe hybridized with all fungal DNAs tested, whereas the second was demonstrated to be a *C. albicans*-specific sequence.

Conserved sequences within repeat regions are attractive targets for PCR-based detection methods because the genome contains multiple copies, thus increasing the proportion of target DNA. If such regions also contain species-specific sequences, the juxtaposition of conserved and unique sequences may enable the coamplifcation of fragments to identify both genus and species in a single PCR.

This invention provides a unique set of primers and an EcoRV-NspI probe useful for the detection of a variety of strains of *C. albicans* and *C. stellatoidea*.

BRIEF DESCRIPTION OF THE INVENTION

This invention relates to an isolated DNA having the sequence selected from the group of sequences given herein as SEQ. ID. NO: 1, SEQ. ID. NO: 2, SEQ. ID. NO: 3, SEQ. ID. NO: 4 and SEQ. ID. NO: 5. In a further embodiment the invention relates to a nucleic acid probe capable of selectively hybridizing to *C. albicans* and *C. stellatoidea* nucleic acids, said probe comprising a sequence selected from the group of sequences given herein as SEQ. ID. NO: 1, SEQ. ID. NO: 2, SEQ. ID. NO: 3, SEQ. ID. NO: 4 and SEQ. ID. NO: 5. and selectively hybridizing fragments thereof. In a further embodiment the invention relates to a method for identifying *C. albicans* and *C. stellatoidea* comprising:(a) isolating DNA from a sample containing said *C. albicans* or *C. stellatoidea*; (b) contacting said DNA with oligonucleotide primers consisting of the two single-stranded oligonucleotides SEQ. ID. NO: 3 as a 5' primer and SEQ. ID. NO: 4 as a 3' primer; (c) amplifying said DNA to form an amplified product; and (d) detecting the amplified product wherein the presence of the amplified product indicates the presence of *C. albicans* or *C. stellatoidea*. In a further embodiment the invention relates to amplification primer pairs comprising the sequences given herein as SEQ. ID. NO: 3 as a 5' primer and SEQ. ID. NO: 4 as a 3' primer and a set of amplification primer pairs having one or more of the 5' primer sequences represented by SEQ. ID. NO: 3 and one or more of the 3' primer sequences represented by SEQ. ID. NO: 4. In yet another embodiment the invention relates to a kit for the detection of *C. albicans* and *C. stellatoidea* comprising a carrier adapted to contain in close confinement therein a first container containing a hybridization solution and a second container containing a probe comprising a sequence selected from the group of sequences given herein as SEQ. ID. NO: 1, SEQ. ID. NO: 2, SEQ. ID. NO: 3, SEQ. ID. NO: 4 and SEQ. ID. NO: 5, and selectively hybridizing fragments thereof. In another embodiment the invention relates to a method of detecting C. albicans or C. stellatoidea nucleic acid in a nucleic acid sample comprising:(a) contacting an oligonucleotide probe to the nucleic acid sample under hybridization conditions wherein said probe comprises a sequence selected from the group of sequences given herein as SEQ ID NO: 1, SEQ ID NO: 2, SEQ. ID. NO: 3, SEQ. ID. NO: 4 and SEQ. ID. NO: 5, and selectively hybridizing fragments thereof; and (b) detecting whether or not said oligonucleotide probe hybridized with the nucleic acid in the sample indicating the nucleic acid in the sample contains C. albicans or C. stellatoidea nucleic acid.

BRIEF DESCRIPTION OF THE FIGURES

FIG. 3 illustrates:

(A) The repeat sequences of this invention aligned to derive a consensus sequence.

(B) Amino acid translations of tandem repeat sequence. Subsitutions in the sequence are indicated by double-underlined residues. In both (A) and (B) the top line of the consensus are those positions that are identical in all ten copies of the repeat. The lower line includes positions that are identical in nine of the ten repeats.

Figure 1:
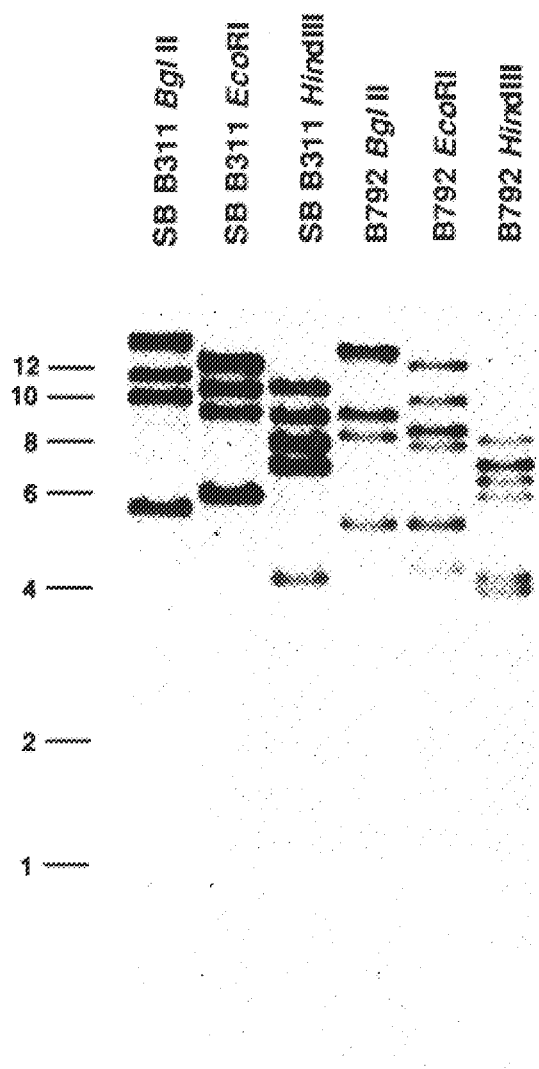
FIG. 1 illustrates a Southern blot of genomic DNA from C. albicans strains SB B311 and B792 digested with a variety of restriction enzymes and probed with EcoRV-NspI fragment of pLH13.
Figure 2:
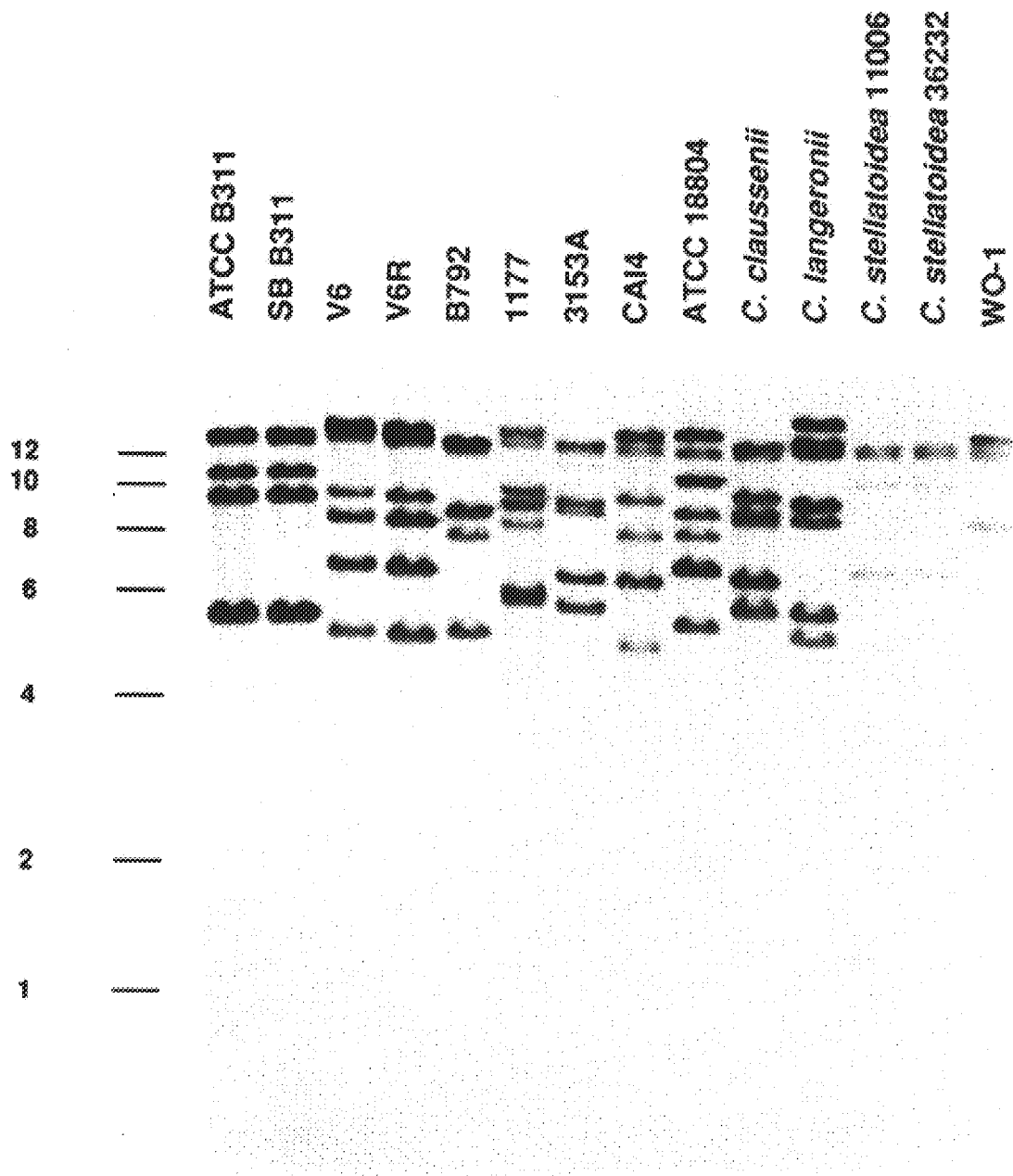
FIG. 2 illustrates a Southern blot of genomic DNA from a variety of Candida species digested with Bg1II and hybridized with the EcoRV-NspI tandem repeat probe.
Figure 4:
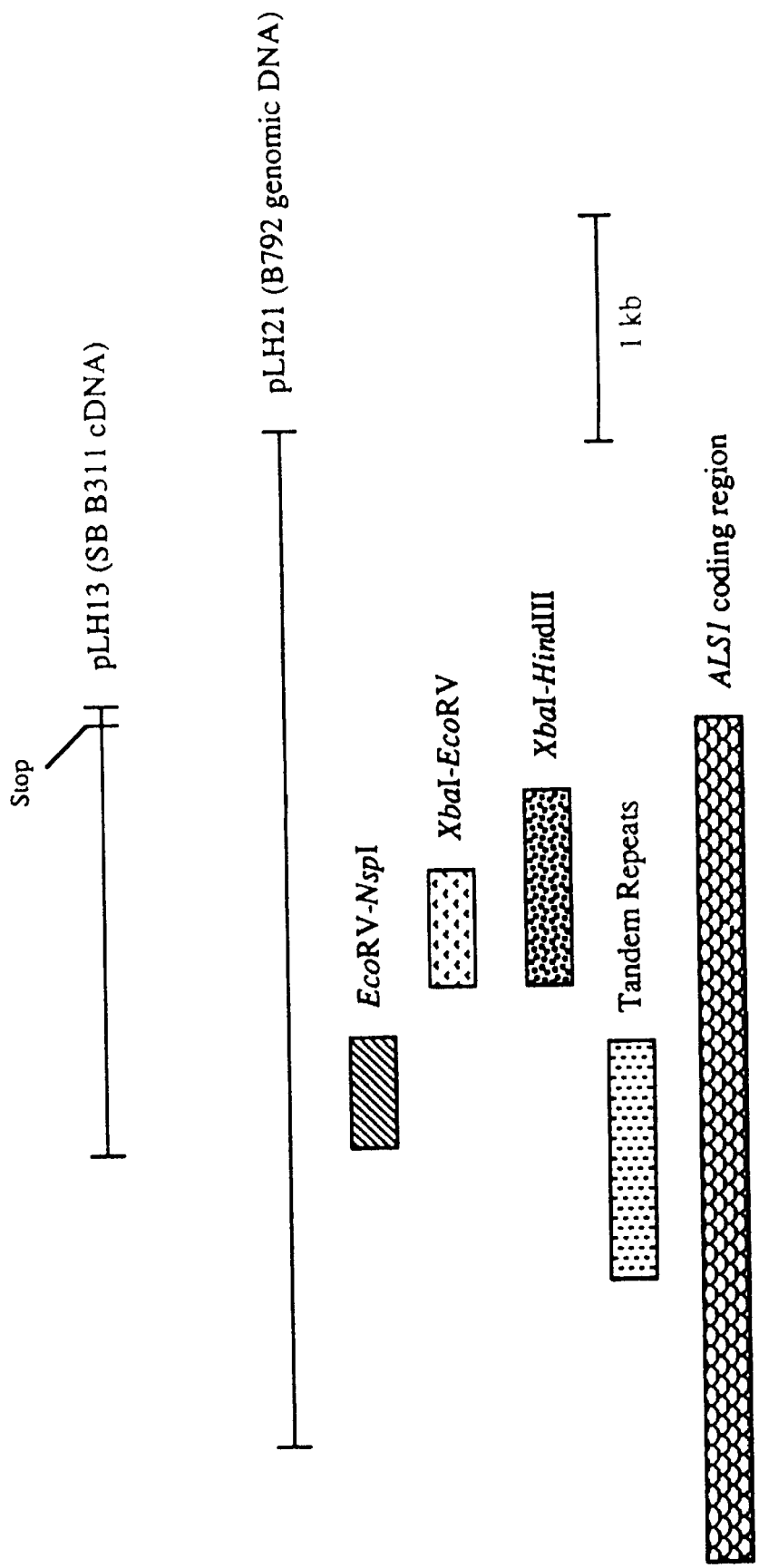

FIG. 4 illustrates restriction maps of clones containing ALS1 coding sequences and their relationship to each other. The EcoRV site of the EcoRV-NspI probe is in the polylinker of pBluescript vector of pLH13.

FIG. 5 illustrates various DNA sequences useful in the practice of this invention. Sequences identified as SEQ ID Nos: 1–5 are presented.

DETAILED DESCRIPTION OF THE INVENTION

The present invention advantageously provides both probes and primers which bind to a variety of strains of C. albicans and C. stellatoidea. General probes are useful as an initial screen for Candidal infection, and provide a rapid alternative to the culturing techniques currently employed as an initial screen, which require on the order of days to weeks of culturing. Once a positive result on the initial screen is found, the species specific probes can be employed, if necessary, to provide a rapid means to diagnose the particular infection.

Nucleotide sequences are presented herein by single strand only, in the 5' to 3' direction, from left to right. One letter nucleotide symbols used herein have their standard meaning in the art in accordance with the recommendations of the IUPAC-IUB Biochemical Nomenclature Commission and the Patent Office Rules.

The term "Candida" as used herein has its conventional meaning in the art (See generally B. Davis et al., Microbiology, 995–96 (2d Ed. 1973). By way of example, the Candida include, but are not limited to, C. albicans, C. claussenii, C. langeronii, C. stellatoidea, C. glabrata, C. gulliermondi, C. keyfr, C. krusei, C. lusitaniae, C. parapsilosis. C. tropicalis and C. viswanathii.

The term "amplification pair," as used herein, refers to a pair of oligonucleotide probes of the present invention selected to be suitable for use together in amplifying a selected Candida nucleic acid sequence by a process such as polymerase chain reaction, ligase chain reaction, or strand displacement amplification, as explained in greater detail below.

Nucleic acid (i.e., DNA or RNA) samples for practicing the present invention may be obtained from any suitable source. Typically, the nucleic acid sample will be obtained in the form of a sample of a biological fluid or biological tissue suspected of containing Candida. Suitable biological fluids include, but are not limited to, sputum, bronchial washings, gastric washings (containing swallowed sputum), blood, milk, and lymph fluid. Suitable tissue samples include, but are not limited to, skin and soft tissue samples. As Candida infect both human and animal species, the present invention is applicable to both human and veterinary diagnostic procedures, and samples may be collected from both human and animal species. Oligonucleotide primers and probes of the present invention may be of any suitable length, depending on the particular assay format employed. In general, the oligonucleotide primers are at least 10 to 30 nucleotides in length. For example, oligonucleotide primers used for detecting Candida are preferably 15 to 20 nucleotides in length. The oligonucleotide probes may incorporate the elements of strand displacement amplification pairs of oligonucleotide probes and are preferably 50 to 150 nucleotides in length.

With respect to nucleic acid sequences which hybridize to specific nucleic acid sequences disclosed herein, hybridization may be carried out under conditions of reduced stringency, medium stringency or even stringent conditions (e.g., conditions represented by a wash stringency of 0.5× SSC and 0.1% SDS at a temperature of 20 or 30 degrees below the melting temperature of the probe, or even conditions represented by a wash stringency of 0.1× SSC and 0.1% SDS at a temperature of 10 degrees below the melting temperature of the DNA sequence to target DNA) in a standard hybridization assay. See J. Sambrook et al., Molecular Cloning, A Laboratory Manual (2d Ed. 1989) (Cold Spring Harbor Laboratory). In general, nucleic acid sequences which hybridize to the DNA disclosed herein will have at least 65% sequence similarity, 70% sequence similarity and even 75% or greater sequence similarity with the sequence of DNA disclosed herein.

Probes of the invention can be utilized with naturally occurring sugar-phosphate backbones as well as modified backbones including phosphorothioates, dithionates, alkyl phosphonates and α-nucleotides. Modified sugar-phosphate backbones are generally illustrated by Miller and T'so, Ann. Reports Med. Chem., 23:295 (1988) and Moran et al., Nuc. Acids Res., 14:5019 (1987). Probes of the invention can be constructed of either ribonucleic acid (RNA) or deoxyribonucleic acid (DNA), with DNA preferred.

Use of the probes in detection methods include Northern blots (RNA detection), Southern blots (DNA detection), western blots (protein detection), and dot blots (DNA, RNA or protein),as discussed above. Other detection methods include kits containing probes on a dipstick setup and the like.

To detect hybrid molecules formed from using the probes of the invention, typically an analytically detectable marker is added to one of the probes. Probes can be labeled by several methods. Probes can be radiolabelled and detected by autoradiography. Such labels for autoradiography include $^3$H, $^{125}$I, $^{35}$S, $^{14}$C, and $^{32}$P. Typically the choice of radioactive isotopes depends on research preferences involving ease of synthesis, stability, and half lives of the isotopes. Other detectable markers include ligands, fluorophores chemiluminescent agents, electrochemical via sensors, time-resolved fluorescence, enzymes, and antibodies. For example, an antibody can be labelled with a ligand. Other detectable markers for use with probes of the invention include biotin, radionucleotides, enzyme inhibitors, co-enzymes, luciferins, paramagnetic metals, spin labels, and monoclonal antibodies. The choice of label dictates the manner in which the label is bound to the probe.

Radioactive nucleotides can be incorporated into probes of the invention by several means. Such means include nick translation of double-stranded probes, copying single-stranded M13 plasmids having specific inserts with the Klenow fragment of DNA polymerase I of *E. coli* or other such DNA polymerase in the presence of radioactive dNTP, transcribing cDNA from RNA templates using reverse transcriptase in the presence of radioactive dNTP, transcribing RNA from vectors containing strong promoters such as SP6 promoters or T7 promoters using SP6 or T7 RNA polymerase in the presence of radioactive rNTP, tailing the 3' ends of probes with radioactive nucleotides using terminal transferase, and by phosphorylation of the 5' ends of probes using gamma $^{32}$P ATP and polynucleotide kinase.

Amplification of a selected, or target, nucleic acid sequence may be carried out by any suitable means. See generally, D. Kwoh and T. Kwoh, *Am. Biotechnol. Lab,* 8: 14–25(1990). Examples of suitable amplification techniques include, but are not limited to, polymerase chain reaction, ligase chain reaction, strand displacement amplification, transcription-based amplification (See: D. Kwoh et al., *Proc. Nat'l. Acad. Sci. USA* 86: 1173–1177 (1989)), self-sustained sequence replication (See: J. Guatelli et al., *Proc. Natl. Acad. Sci. USA* 87: 1874–1878 (1990)), and the Qβ replicase system (See: P. Lizardi et al., *BioTechnology* 6: 1197–1202 (1988)).

Polymerase chain reaction (PCR) is carried out in accordance with known techniques. See, e.g.,: U.S. Pat. Nos. 4,683,195; 4,683,202; 4,800,159; and 4,965,188 (the disclosure of all U.S. Patent references cited herein are to be incorporated herein by reference). In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques.

Ligase chain reaction (LCR) is carried out in accordance with known techniques. See, e.g.,: R. Weiss, *Science* 254: 1292 (1991). In general, the reaction is carried out with two pairs of oligonucleotide probes; one pair binds to one strand of the sequence to be detected; the other pair binds to the other strand of the sequence to be detected. Each pair together completely overlaps the strand to which it corresponds. The reaction is carried out by, first denaturing (e.g., separating) the strands of sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Strand displacement amplification (SDA) is also carried out in accordance with known techniques. See: G. Walker, et al., *Proc. Nat'l. Acad. Sci. USA* 89: 392–396 (1992); G. Walker et al., *Nucleic Acids Res.* 20: 1691–1696(1992). SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., oligonucleotide probe of the present invention) which hybridizes to the target sequence to be amplified and/or detected. The flanking sequence, which simply serves to facilitate binding of the restriction enzyme to the recognition site is preferably about 15 to 20 nucleotides in length; the restriction site is functional in the SDA reaction (i.e., phosphorothioate linkages incorporated into the primer strand do not inhibit subsequent nicking—a condition which may be satisfied through use of a nonpalindromic recognition site); the oligonucleotide probe portion is preferably about 13 to 15 nucleotides in length. SDA is carried out with a single amplification primer as follows: a restriction fragment (preferably about 50 to 100 nucleotides in length and preferably of low GC content) containing the sequence to be detected is prepared by digesting a DNA sample with one or more restriction enzymes, the SDA amplification primer is added to a reaction mixture containing the restriction fragment so that a duplex between the restriction fragment and the amplification primer is formed with a 5' overhang at each end, a restriction enzyme which binds to the restriction site on the amplification probe (e.g., HincII) is added to the reaction mixture, an exonuclease deficient DNA polymerase (e.g. an exonuclease deficient form of *E. coli* DNA polmerase I, See: V. Derbyshire, *Science* 240: 199–201 (1988)) is added to the reaction mixture, and three dNTPs and one dNTP(αS), with the dNTP[αS] selected so that a phosphorothioate linkage is incorporated into the primer strand at the restriction site for the particular restriction enzyme employed (e.g., dGTP, dCTP, dTTP, amd dATP[αS] when the restriction enzyme is HincII) are added to the reaction mixture. The DNA polymerase extends the 3' ends of the duplex with the dNTPs to form a downstream complement of the target strand, the restriction enzyme nicks the restriction site on the amplification primer, and the DNA polymerase extends the 3' end of the amplification primer at the nick to displace the previously formed downstream complement of the target strand. The process is inherently repetitive because the restriction enzyme continuously nicks new complementary strands as they are formed from the restriction site, and the DNA polmerase continuously forms new complementary strands from the nicked restriction site. SDA can be carried out with a pair of primers on a double stranded target DNA sequence, with the second primer binding to the 5' end of the complementary strand, so that two sets of repetitive reactions are occurring simultaneously, with the process proceeding exponentially because the products of one set of reactions serve as target for the amplification primer in the other set of reactions. In addition, the step of first digesting the DNA sample to form a restriction fragment can be eliminated by exploiting the strand displacing activity of the DNA polymerase and adding a pair of "bumper" primers which bind to the substrate at a flanking position 5' to the position at which each amplification primer binds. Each bumper primer extension product displaces the corresponding amplification primer extension product, and the two displaced, complementary, amplification primer extension products bind to one another to form a double-stranded DNA fragment which can the serve as a substrate for exponential SDA with that pair of SDA primers.

When SDA is employed, the oligonucleotide probes of the invention are preferably selected so that guanine plus cytosine content is low, preferably comprising less than 70% of the total nucleotide composition of the probe. Similarly, the target sequence should be of low GC content to avoid the formation of secondary structures.

A kit for detecting Candida nucleic acid in a nucleic acid sample contains at least one probe of the present invention, and hybridization solution for enabling hybridization between the probes and the nucleic acid sample, with the probe either suspended in the solution or provided separately in lyophilized form. One example of a suitable hybridization solution is a solution comprised of 6× SSC (0.9M sodium chloride. 0.09M sodium citrate, pH 7.0), 0.1M EDTA pH 8.0, 5× Denhardt's solution [0.1% (w/v) Ficoll Type 400, 0.1% (w/v) polyvinylpyrrolidone, 0.1% (w/v) bovine serum albumin], and 100 µg/ml sheared, denatured salmon sperm DNA, commercially available from Bethesda Research Laboratories, Gaithersburg, Md. 20877 USA under Catalog No. 5565UA. See also T. Maniatis et al., Molecular Cloning: A Laboratory Manual, 387–388 (1982) (Cold Spring Harbor Laboratory). The components of the kit are packaged together in a common container (e.g., a container sealed with a frangible seal), the kit typically including an instruction sheet for carrying out a specific embodiment of the method of the present invention. Additional optional components of the kit, depending on the assay format to be employed, include a second probe for carrying out PCR as explained above (or, in the case of a kit for carrying out a detecting step (e.g., a probe of the invention labelled with a detectable marker and optionally an enzyme substrate when the detectable marker is an enzyme).

EXAMPLE

In response to certain environmental stimuli, yeast-form cells of *C. albicans* undergo a transition to growth as filamentous hyphal forms. A cDNA library constructed from mRNA isolated during this transition was screened by differential hybridization using yeast (YEPD)-and hyphal (RPMI)-specific probes. This type of screen should reveal both hyphal-specific genes as well as genes expressed in response to media components and culture conditions. One clone, clone pLH13 which contains one genomic example of the tandem repeat region from *Candida albicans* strain SB B311, was originally isolated due to it differential expression in an assay designed to detect hyphal-specific cDNA clones. Through collaborative work, it is now known that pLH13 encodes a portion of the ALS1 gene of *C. albicans*; expression of ALS1 is regulated by a component of the tissue culture medium RPMI 1640 rather than by hyphal formation. (Hoyer, L L et al., *Mol. Micro.* 15(1): 39–54 (1995). DNA sequencing of pLH13 revealed a 2000 bp insert. At the 5' end of this insert were multiple head-to-tail copies of a 108-bp sequence. While polymorphisms are present between adjacent copies of the 108-bp sequence, a basic consensus sequence was derived for this region. An EcoRV-NspI probe was isolated from pLH13; this DNA fragment resides at the 5' end of the pLH13 insert and contains the extent of the tandem repeat sequences from pLH13 and only 12 bp of additional sequence 3' of the repeats. Southern blots of genomic *C. albicans* DNA revealed this sequence is found on multiple genomic fragments. Depending on the restriction enzyme used in this analysis, as many as 7 different genomic fragments hybridize to the EcoRV-NspI probe.

A second clone, pLH21, was isolated from a library of *C. albicans* strain B792 genomic DNA via hybridization to sequences found in pLH13. Clone pLH21 contains all of the sequence information found in pLH13 as well as approximately 1.5 kb of additional sequence 5' of the tandem repeat region. DNA sequencing of pLH21 revealed that the exact sequence of the tandem repeats varies between strains SB B311 and B792, but that the consensus sequence is minimally 60% to 70% conserved between individual copies of the 108-bp repeated sequence both within the same strain and between *C. albicans* strains. Northern blot analysis of *C. albicans* RNA indicated that two RNA species hybridize to the EcoRV-NspI probe suggesting the possibility of more than one expressed gene containing the tandem repeat sequences. The multiplicity of genomic fragments hybridizing to the same probe in Southern blots (see above) suggests there are instances of the tandem repeats in the *C. albicans* genome that are not present in expressed genes.

Serial passage experiments (where cells from a single colony were grown for 530 generations) indicated that the tandem repeats are relatively stable in the *C. albicans* genome. No change in the pattern of restriction fragments hybridizing with the EcoRV-NspI probe was observed when DNA from the "zero" generation was compared with DNA from cells of generation 530. This is important since certain repeated sequences in *C. albicans* have been shown to be unstable (Scherer and Stevens, *Proc. Nat'l Acad. Sci. USA* 85:1452–1456) (1992)). Stability of this repeated sequence makes it a more predictable target for PCR detection.

Southern blots of genomic DNA from a variety of Candida species, both pathogenic and non-pathogenic, were hybridized with the EcoRV-NspI probe to determine if the tandem repeat motif was unique to *C. albicans* or a feature of many Candida species. Hybridization signals were observed for all *C. albicans* strains tested, and Type I *C. stellatoidea*. Through collaborative work, the tandem repeats were also detected in *C. claussenii* and *C. langeronii*. Although they were originally assigned as different species, *C. claussenii* and *C. langeronni* have recently been demonstrated to be "synonyms" of *C. albicans* (Wickes et al., *J. Gen. Microbiol.* 138:901–907 (1992)). Among the Candida species tested and found to not contain DNA sequences that hybridize to the EcoRV-NspI tandem repeat probe are *C. glabrata, C. guilliermondii, C. keyfr, C. krusei, C. lusitaniae, C. parapsilosis, C. tropicalis,* and *C. viswanathii*. *Saccharomyces cerevisiae* genomic DNA was also tested and did not hybridize with the EcoRV-NspI probe. Therefore, the tandem repeat sequences constitute a specific probe that detects *C. albicans* and *C. stellatoidea*.

Experimental procedures

Strains and media

Yeast strains used in this study are listed in Table 1. Library construction and screening were performed using *C. albicans* B311 maintained in the SmithKline Beecham (SB) culture collection. Because strains called B311 have been demonstrated to vary widely (Mackenzie and Odds, *J. Med. Vet. Mycol.* 29:255–61 (1991)), strain B311 (ATCC 32354) was obtained from the American Type Culture Collection. Subsequent comparisons between ATCC B311 and SB B311 indicated they are identical with respect to the coding regions for repeat regions from which the primers and probes of this invention are generated.

Cells of *E. coli* strain DH5αMCR (Gibco BRL) containing various plasmids were grown in Luria broth or on Luria agar plates (1.5% (w/v) agar) supplemented with 100 μg ml$^{-1}$ ampicillin (Sambrook et al., Molecular Cloning: A Laboratory Manual, Cold Spring Harbour Laboratory New York (1989)). For genomic DNA isolations, *S. cerevisiae* and Candida strains were grown in yeast extract/peptone/dextrose (YEPD; Sherman et al., ("Lab Course Manual for Methods in Yeast Genetics" Cold Spring Harbor, New York (1986))

*C. albicans* yeast forms were grown in YEPD at 30° C. Hyphal induction for cDNA library construction was accomplished by transferring yeast cells from YEPD to the defined tissue culture medium RPMI 1640 with L-glutamine (RPMI; Gibco BRL catalogue number 11875) at 37° C. and 5% $CO_2$. *C. albicans* cells were also grown in synthetic complete yeast medium (SC; Hicks and Herskowitz, *Genetics* 83: 245–58 (1976)) and the defined medium described by Lee et al. *Sabouraudia* 13: 148:153 (1975) in which hyphal growth is induced by changes in pH and/or temperature.

TABLE 1

YEAST STRAINS

| Organism | Source/Reference |
|---|---|
| *C. albicans* | |
| ATCC B311 (ATCC 32354) | ATCC |
| SB B311 | SmithKline Beecham Corporation |
| V6 | Buckley, et al., Infect. and Immun. 37:1209–1217 (1982) |
| V6R | Buckley, et al., Infect. and Immun. 53:13–15 (1986) |
| B792 | J. A. Gorman, Bristol-Myers Squibb |
| 1177 (CBS 5736) | S. Scherer |
| 3153A (ATCC 36801) | ATCC |
| CA14 | Fonzi and Irwin, Genetics 134:717–728 (1993) |
| WO-1 | Slutsky, et al., J. Bacteriol. 169:189–197 (1987) |
| ATCC 18804 (Type culture) | ATCC |
| *C. claussenii* (ATCC 18814) | ATCC |
| *C. langeronii* (ATCC 22972) | ATCC |
| *C. stellatoidea* | |
| ATCC 11006 (Type Culture) | ATCC |
| ATCC 36232 | ATCC |
| *C. glabrata* | C. Frey, SmithKline Beecham |
| *C. guilliermondii* | C. Frey |
| *C. Keyfr* (ATCC 46764) | ATCC |
| *C. krusei* | C. Frey |
| *C. lusitaniae* | C. Frey |
| *C. parapsilosis* | C. Frey |
| *C. tropicalis* | C. Frey |
| *C. viswanathii* (ATCC 22981) | ATCC |

DNA manipulations and transformations

Plasmid DNA was recovered from *E. coli* by alkaline lysis (Birnboim and Doly, *Nucl. Acid Res.* 7:1513–1523 (1979)). Genomic DNA from *C. albicans* and *S. cerevisiae* was prepared using the method of Sherman et al., supra (1986). Competent *E. coli* cells were prepared according to Stoker et al. In: Transcription and Translation: A practical approach, Oxford IRL Press pp. 153–77 (1984).

Construction and screening of transition-specific cDNA Library

*C. albicans* SB B311 was grown at 25° C. in YEPD to mid-log phase. All cells from this culture exhibited yeast morphology; approximately 55% of cells contained buds. Cells were harvested, washed twice in sterile water and inoculated into RPMI 1640 with L-glutamine at $1.5 \times 10^6$ cell ml$^{-1}$ to stimulate hyphal formation. This culture was incubated at 37° C. and 5% $CO_2$ for 20 min. At this point in the transition between yeast and hyphal growth, germ tubes were not visible microscopically, although cells observed in a parallel culture subsequently formed germ tubes at approximately 2 h with hyphal elongation apparent at 3–4 h. Total RNA was prepared (Carlson and Botstein, *Cell* 28:145–154 (1982)) and polyA$^+$ RNA selected (Aviv and Leder, *Proc. Nat'l Acad. Sci. USA* 69:1408–12 (1972)). PolyA$^+$ RNA was used for cDNA synthesis according to manufacturer's protocols (Boehringer Mannheim) with a random primer. Blunt-ended cDNA was ligated first to EcoRI/NotI linkers (Invitrogen) and then into EcoRI-digested Lambda ZAP II phage arms (Stratagene). Ligated phage were packaged using Gigapack II Gold packaging extracts (Stratagene) and plated on XL1-Blue cells following supplied protocols (Stratagene). The transition-specific cDNA library contained approximately $0.5 \times 10^6$ clones.

Single-stranded cDNA probes were synthesized (Sambrook et al., supra 1989) using RNA from mid-log, YEPD-grown cells of strain SB B311 (yeast-specific probe) and RNA from SB B311 cells grown in RPMI 1640 at 37° C. and 5% $CO_2$ for 16 h (hyphal-specific probe). After 16 h in RPMI, cells of strain SB B311 had formed extensive mats of long, branching hyphae with fewer than 5% exhibiting lateral buds. Duplicate lifts of the transition-specific library (with approximately 1000 phage per plate) were prepared using standard procedures (Sambrook et al., supra 1989). Following prehybridization in 50% formamide (Sambrook et al., supra 1989) for at least 2 h, boiled single-stranded cDNA probes were added. Following overnight hybridization at 42° C., filters were washed four times for 15 min in 0.1× SSC, 0.1% SDS at 46° C. before exposure to film.

Verification of selected clones

Phagemids were excised from selected clones according to supplied protocols (Stratagene). Phagemid DNA was digested with NotI, which cuts in the linkers used in library construction, to release the insert fragment. These digests were run on 1% agarose gels which were prepared for Southern blotting and transferred to nitrocellulose membranes using standard procedures (Sambrook et al., supra 1989). Single-stranded cDNA probes were again prepared from yeast and hyphal RNA and hybridized to the membranes. One clone (pLH13) was identified because of tis intense signal when hybridized with the hyphal-specific probe and no signal when hybridized with the yeast-specific probe.

Construction of genomic libraries

Genomic DNA, completely digested with one or a combination of restriction enzymes, was run on 1% agarose/TAE gels (Sambrook et al., supra 1989). Restriction fragments of the size previously defined by Southern blotting to hybridize with probes derived from pLH13 were excised from the gel and purified with GeneClean (Bio 101). These fragments were ligated into similarly digested pUC18 or pUC19 (59). Ligation mixes were transformed into *E. coli* DH5αMCR using the method of Hanahan J. Mol. Biol. 166:557–580 (1983). Transformants were plated and colonies screened using $^{32}$P-labelled probes (Sambrook et al., supra 1989).

DNA sequencing and sequence analysis

The majority of DNA sequencing was performed by the dideoxy termination method (Sanger et al., *Proc. Nat'l Acad. Sci. USA* 74: 5463–5467 (1977)), using a Sequenase kit (US Biochemical), and [$^{35}$S]-dATP (New England Nuclear). DNA sequencing of the 5'-most portion of the gene was accomplished on an Applied Biosystems Model 373A sequencer using either dye primer or dye terminator chemistry. Sequencing was facilitated by construction of subclones in pUC18 and pUC19 vectors (Yanisch-Perron et al., *Gene* 33: 103–119 (1985)) or by construction of nested deletions using the Double-Stranded Nested Deletion Kit (Pharmacia). Custom oligonucleotide primers were synthesized to complete the DNA sequence on both strands. Double-stranded template DNA was prepared according to Kraft et al. *Biotechniques* 6:544–47 (1988). DNA and protein sequences were analysed using GCG software (Devereux et al., *Nuc. Acid Res.* 12:387–395 (1984)); the GenBank database (Release 82; April 1994) and SwissProt database (Release 26, July 1993) were searched. The PROSITE database was accessed using the MOTIFS program of GCG software (Devereux et al., supra 1984).

Genomic Southern blots

Genomic DNA (5 μg per lane) was digested with restriction enzymes according to the specifications of the manufacturer and run on agarose gels of 0.6% of 1.0% in TAE buffer (Sambrook et al., supra 1989). Gels were processed (Sambrook et al., supra 1989) and blotted overnight onto MagnaGraph nylon transfer membranes (MSI). Prehybridization, hybridization and signal detection were done according to Genius System User's Guide (Boehringer Mannheim). Membranes were exposed to Kodak X-OMat film and developed.

Northern blots

Total RNA was isolated according to the protocol of Wise In: Guide to Yeast Genetics and Molecular Biol. Academic Press, San Diego pp. 405–415 (1991). Samples were loaded onto formaldehyde agarose gels and run in a buffer consisting of 20 mM morpholinopropane sulphate (MOPS) pH 7.0, 5 mM sodium acetate and 1 mM EDTA at no more than 40 mA constant current. Gels were soaked in deionized water and 20× SSC (Sambrook et al., supra 1989) prior to blotting onto nitrocellulose.

Probes were prepared by random priming using the Pharmacia OligoLabelling Kit and [$^{32}$P]-dCTP (3000 Ci mmol$^{-1}$ ICN). Hybridizations were carried out at 42° C. in 50% (v/v) formamide (Sambrook et al., supra 1989). Blots were washed in 0.5× SSC/0.1% SDS at 60° C. *C. albicans* CYP1 (Koser et al., Gene 96:189–195 (1990)) or a fragment of *C. albicans* TEF1 (Sundstrom et al., *J. Bacteriol.* 172:2036–2045 (1990)) isolated by PCR (see below) were used as positive controls.

PCR conditions

A fragment of *C. albicans* TEF1 was isolated by PCR amplification for use as a positive control on Northern blots. This gene was chosen since it was previously shown to be expressed equally in both the yeast and hyphal forms (Sundstrom et al., supra 1990). PCR primers 5'-CACGTTACCGTCATTGATGC-3' (forward) (SEQ. ID. NO: 6) and 5'-CAACTCTACCGACTGGCACA-3' (reverse) (SEQ. ID NO: 7) were used to amplify a 541 bp product from *C. albicans* SB B311 genomic DNA.

The length of the tandem repeat fragments from a variety of Candida strains was evaluated using PCR. The forward primer 5'-GGTGGTACAAGTTCCACTGCC-3' (SEQ. ID NO: 8), which anneals to the nucleotide sequence immediately 5' of the tandem repeats, and reverse primer 5'-GTTGACATAATGAGGACGGG-3' (SEQ. ID NO: 9), which anneals 70 nucleotides 3' of the end of the tandem repeat segment of ALS1, were used. Products were run on 1% agarose/TAE gels and visualized by ethidium bromide staining.

Serial passage experiments

Two single colonies each of strains SB B311 and B792 were inoculated into individual tubes of YEPD. After overnight incubation, cells were counted and used to inoculate fresh flasks of YEPD. Cells were grown to mid-stationary phase and then counted again from each flask. These values were used to calculate the number of generations each culture had grown. Fresh flasks of YEPD were inoculated and the process was continued. Samples representing each 100 generations of growth were stored in 15% glycerol at −70° C. Each culture was grown for a total of 530 generations. Genomic DNA was prepared from these cultures and digested with a variety of restriction enzymes for analysis on Southern blots.

---

What is claimed is:

1. A method for identifying *C albicans* or *C stelloidea* comprising the steps of:
   (a) isolating DNA from a sample containing said *C albicans* or *C stelloidea*;
   (b) contacting said DNA with oligonucleotide primers consisting of the two single-stranded oligonucleotides SEQ. ID. NO: 3 as the 5' primer and SEQ. ID. NO: 4 as the 3' primer;
   (c) amplifying said DNA to form an amplified product; and
   (d) detecting the amplified product wherein the presence of the amplified product indicates the presence of *C albicans* or *C stelloidea*.

2. The method according to claim 1 wherein the amplification is accomplished by polymerase chain reaction.

3. The method according to claim 1 wherein said detection includes subjecting the amplified product to hybridization with an analytically detectable probe internal to the amplified product.

4. A method of detecting *C albicans* or *C stelloidea* nucleic acid in a nucleic acid sample comprising the steps of:
   (a) contacting an oligonucleotide probe to the nucleic acid sample under hybridization conditions wherein said probe comprises a sequence selected from the group consisting of SEQ ID NO: 3, SEQ ID NO: 4, SEQ ID NO: 5 and oligonucleotide fragments thereof, which oligonucleotide fragments comprise between 10 and 150 contiguous nucleotides of SEQ ID NO: 3, SEQ ID NO: 4, or SEQ ID NO: 5; and
   (b) detecting whether or not said oligonucleotide probe hybridized with the nucleic acid in the sample indicating the nucleic acid in the sample contains *C albicans* or *C stelloidea* nucleic acid.

5. The method according to claim 4 wherein said nucleic acid is DNA.

6. The method according to claim 4 wherein said nucleic acid is RNA.

7. The method according to claim 4 wherein said nucleic acid probe is labeled with an analytically detectable marker and wherein said detecting step is carried out by detecting said detectable marker.

8. The method according to claim 4 further comprising a strand displacement amplification step preceeding the detection step.

9. The method according to claim 4 further comprising a polymerase chain reaction amplification step preceeding the detection step.

10. The method according to claim 4 further comprising a ligase chain reaction amplification step preceeding the detection step.

11. A kit for the detection of *C albicans* or *C stelloidea* comprising a carrier adapted to contain in close confinement therein a first container containing a hybridization solution and a second container containing a probe comprising a sequence selected from the group consisting of SEQ ID NO: 2, SEQ ID NO: 3, SEQ ID NO: 4, SEQ ID NO: 5 and oligonucleotide fragments thereof, which oligonucleotide fragments comprise between 10 and 150 contiguous nucleotides of SEQ ID NO: 2, SEQ ID NO: 3, SEQ ID NO: 4, or SEQ ID NO: 5.

12. The kit according to claim 11 optionally containing:
    a third container containing amplification probes and
    additional container containing amplification reagents.

13. The kit according to claim 11 wherein said probe is lyophilized.

14. The kit according to claim 11 wherein said probe is analytically labelled.

15. The kit according to claim 11 wherein the contents of said first container and said second container are combined into a single container.

16. A method for identifying *C albicans* and *C stelloidea* comprising:
    (a) isolating DNA from a sample containing said *C albicans* and *C stelloidea*;
    (b) contacting said DNA with oligonucleotide primers consisting of the two single-stranded oligonucleotides SEQ. ID. NO: 3 as the 5' primer and SEQ. ID. NO: 4 as the 3' primer;
    (c) amplifying said DNA to form an amplified product; and
    (d) detecting the amplified product wherein the presence of the amplified product indicates the presence of *C albicans* and *C stelloidea*.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1071 base pairs
        ( B ) TYPE: nucleic acid
        ( C ) STRANDEDNESS: single ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

| | | | | | | |
|---|---|---|---|---|---|---|
| CCAAATCCAA | CTGTTAGTAC | TACTGAATAT | TGGTCTCAGT | CCTTTGCTAC | AACCACTACA | 60 |
| GTTACTGCTC | CTCCAGGTGG | TACCGATACT | GTGATTATCA | GAGAGCCACC | AAACCATACT | 120 |
| GTCACTACTA | CTGAATATTG | GTCACAATCC | TTTGCTACTA | CTACTACTGT | TACTGCTCCT | 180 |
| CCAGGTGGTA | CTGACTCAGT | AATTATCAGA | GAACCACCAA | ATCCAACTGT | CACTACAACC | 240 |
| GAGTATTGGT | CTCAATCCTT | TGCTACTACT | ACTACAGTTA | CTGCTCCTCC | AGGTGGTACT | 300 |
| GACTCAGTAA | TTATCAGAGA | ACCTCCAAAC | CCAACTGTCA | CCACCACTGA | ATATTGGTCC | 360 |
| CAATCTTACG | CAACCACAAC | TACTGTGACT | GCTCCTCCAG | GAGGCACTGA | CTCAGTAATT | 420 |
| ATCAGAGAAC | CACCAAACCA | CACTGTCACT | ACTACTGAAT | ACTGGTCACA | ATCATATGCC | 480 |
| ACCACTACCA | CTGTAACTGC | ACCACCAGGT | GGTACTGACA | CTGTTATCAT | TAGAGAGCCA | 540 |
| CCAAACCACA | CTGTCACTAC | TACTGAGTAT | TGGTCTCAAT | CGTTTGCTAC | TACCACAACT | 600 |
| GTAACTGGTC | CACCAAGTGG | CACTGATACT | GTTATCATTA | GGGAACCACC | AAACCCAACT | 660 |
| GTCACCACTA | CTGAATACTG | GTCTCAATCA | TATGCAACCA | CTACTACCAT | TACCGCTCCA | 720 |
| CCTGGTGAAA | CTGATACCGT | TCTCATCAGA | GAGCCACCAA | ACCATACTGT | CACTACTACT | 780 |
| GAATACTGGT | CTCAATCATA | TGCTACAACC | ACCACTGTTA | CTGCACCACC | TGGTGAAACC | 840 |
| GATACCGTTC | TTATCAGAGA | GCCACCAAAC | CATACTGTCA | CTACTACTGA | ATACTGGTCT | 900 |
| CAATCATATG | CTACAACCAC | CACTGTTACT | GCACCACCAG | GTGGTACCGA | TACTGTTATC | 960 |
| ATTAGAGAGC | CACCAAATCC | AACAGTTACT | ACTACTGAAT | ATTGGTCACA | ATCATTTGCC | 1020 |
| ACAACCACCA | CAGTTACTGC | TCCTCCAGGT | GGTACTGACA | CTGTGATTAT | C | 1071 |

( 2 ) INFORMATION FOR SEQ ID NO:2:

( i ) SEQUENCE CHARACTERISTICS:
              ( A ) LENGTH: 108 base pairs
              ( B ) TYPE: nucleic acid
              ( C ) STRANDEDNESS: single
              ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

| | | | | | | |
|---|---|---|---|---|---|---|
| CCAAAYCMHA | CWGTYASYAC | HACYGARTAY | TGGTCNCART | CNTWYGCHAC | HACHACHACH | 60 |
| RTDACYGSWC | CWCCWRGWRG | HACYGAYWCH | GTDMTYATYA | GRGARCCW | | 108 |

( 2 ) INFORMATION FOR SEQ ID NO:3:

( i ) SEQUENCE CHARACTERISTICS:
              ( A ) LENGTH: 20 base pairs (B) TYPE: nucleic acid
    (C) STRANDEDNESS: single
    (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CCAAAYCMHA CWGTYASYAC 20

(2) INFORMATION FOR SEQ ID NO:4:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

WGGYTCYCTR ATRAKHACDG 20

(2) INFORMATION FOR SEQ ID NO:5:

(i) SEQUENCE CHARACTERISTICS:
    (A) LENGTH: 425 base pairs
    (B) TYPE: nucleic acid
    (C) STRANDEDNESS: single
    (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GATATCGAAT TCGCGGCCGC GTCACAATCA TATGCCACCA CTACCACTGT AACTGCACCA 60

CCAGGTGGTA CTGACACTGT TTATCATTAG AGAGCCACCA AACCATACTG TCACCACTAC 120

TGAATACTGG TCTCAGTCCT ATGCAACCAC TACTACCATT ACCGCTCCAC CTGGTGAAAC 180

CGATACCGTT CTTATCAGAG AGCCACCAAA CCATACTGTC ACTACTACTG AATACTGGTC 240

TCAATCATAT GCTACAACCA CCACTGTTAC TGCACCACCA GGAGGTACCG ATACTGTTAT 300

CATTAGAGAG CCACCAAATC CAACAGTTAC TACTACTGAA TATTGGTCAC AATCATTTGC 360

CACAACCACC ACAGTTACTG CTCCTCCAGG TGGTACTGAC ACTGTGATTA TCTATGAAAG 420

CATGT 425

(2) INFORMATION FOR SEQ ID NO:6:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

CACGTTACCG TCATTGATGC     20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

CAACTCTACC GACTGGCACA     20

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

GGTGGTACAA GTTCCACTGC C     21

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

GTTGACATAA TGAGGACGGG                                                                                    20